United States Patent [19]

Russell, Jr. et al.

[11] Patent Number: 4,702,228
[45] Date of Patent: Oct. 27, 1987

[54] X-RAY-EMITTING INTERSTITIAL IMPLANTS

[75] Inventors: John L. Russell, Jr., Alpharetta; David N. Coggins, Atlanta, both of Ga.

[73] Assignee: Theragenics Corporation, Atlanta, Ga.

[21] Appl. No.: 694,941

[22] Filed: Jan. 24, 1985

[51] Int. Cl.⁴ .............................................. A61N 5/10
[52] U.S. Cl. .................................................... 128/1.2
[58] Field of Search ................... 128/1.1, 1.2; 424/1.1, 424/1.5

[56] References Cited

U.S. PATENT DOCUMENTS 3,351,049  4/1965  Lawrence ............................ 128/1.2
4,323,055  4/1982  Kubiatowicz ....................... 128/1.2
4,510,924  4/1985  Gray .................................... 128/1.2

OTHER PUBLICATIONS

The Use of Iodine-125 for Interstitial Implants, U.S. Department of Health, Education, & Welfare, Publication (FDA), Hilaris et al., 76-8022, 1975.
Medical Physics Monograph No. 7, "Recent Advances in Brachytherapy Physics", D. R. Shearer, ed., pub. of Amer. Ass. of Physicists in Medicine.
Walter R. Scott, *Radiology*, 105, 454–455 (1972).

Primary Examiner—Kyle L. Howell
Assistant Examiner—John C. Hanley
Attorney, Agent, or Firm—Fitch, Even, Tabin & Flannery

[57] ABSTRACT

Particles or "seeds" are manufactured for implantation into tumors within a human body for emitting X-rays to destroy or reduce the tumors. The seeds contain palladium which is substantially enriched in palladium-102 and which is activated by exposure to neutron flux so as to contain a minor, but significant, fraction of X-ray-emitting palladium-103. The palladium is distributed on or throughout a base material so as to reduce self-shielding by the palladium. The seeds include an X-ray-opaque marker to facilitate external visualization of the seeds after their implantation, the marker preferably being formed of a material, such as lead or rhodium, which does not activate to contain undesirable isotopes under the radiation conditions in which palladium-102 is activated to palladium-103. The base material-distributed palladium and the marker are encased in an elongated shell which is formed by welding a pair of end caps to a tubular member, the construction of the shell reducing the mass of material at the end of the seed, thereby providing a more isotropic angular distribution of X-rays.

9 Claims, 4 Drawing Figures

U.S. Patent  Oct. 27, 1987  4,702,228
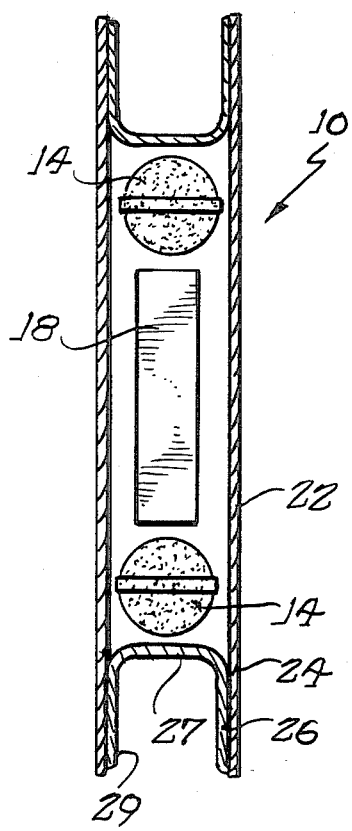
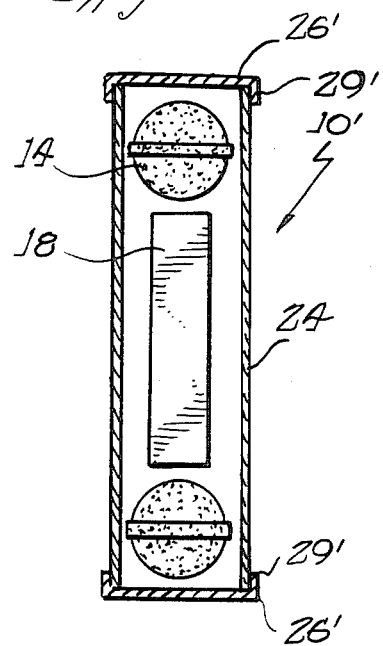
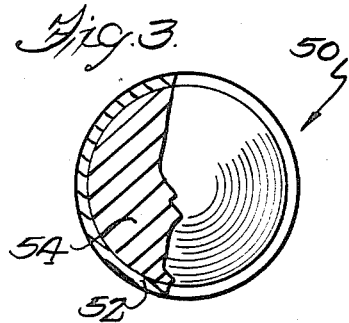
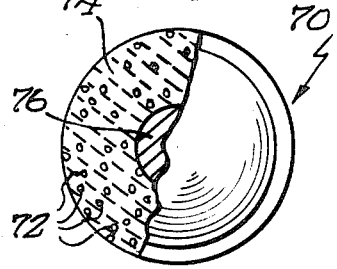

X-RAY-EMITTING INTERSTITIAL IMPLANTS

The present invention is directed to interstitial implantation of X-ray-emitting sources. More particularly the invention is directed to particles or seeds containing palladium-103 as the X-ray-emitting source and to methods of producing capsules or seeds for interstitial implantation.

BACKGROUND OF THE INVENTION

Advantages of interstitial implantation of radiation-emitting material for localized tumor treatment has been recognized for some time now. Interstitially implanted materials concentrate the radiation at the place where this treatment is needed, i.e., within a tumor so as to directly affect surrounding tumor tissue, while at the same time exposing normal tissue to far less radiation than does radiation that is beamed into the body from an external source.

One early implantable radioactive material was gold wire fragments enriched in radiation-emitting gold isotopes, such as gold-198. An advantage of gold wire, for interstitial implantation is that gold is compatible with the body in that it does not degrade or dissolve within the body. Another commonly used implantable material is radon-222.

Materials, such as gold-198 and radon-222, have significant counterindicating characteristics for interstitial tumor treatment in that they emit relatively penetrating radiation, such as X-rays or gamma radiation of higher energy than is preferred, beta particles or alpha particles. Such materials not only subject the patient's normal tissue to more destructive radiation than is desired but expose medical personnel and other persons coming into contact with the patient to significant doses of potentially harmful radiation.

U.S. Pat. No. 3,351,049 describes capsules or seeds in which an enclosed outer shell encases an X-ray-emitting isotope having a selected radiation spectrum. Notably, the capsules contain iodine-125 having a radiation spectrum which is quite favorable for interstitial use compared to previously used materials. The encasing shell localizes the radioactive iodine to the tumor treatment site, preventing the migration of iodine to other parts of the body, notably the thyroid, which would occur if bare iodine were directly placed in the tumor site. The use of an encasing shell permits the use of other X-ray-emitting isotopes which would dissolve in the body or present a toxic hazard to the recipient. Capsules or seeds containing iodine-125 have been used in treating patients for some time now, and their general effectiveness has been described in several publications, for example, *The Use of Iodine-125 for Interstatial Implants*, U.S. Department of Health, Education, and Welfare Publication (FDA) 76-8022, Basil H. Hilaris, et al., November 1975.

Other isotopes have been suggested as alternatives to iodine-125. The '049 patent, in addition to iodine-125, suggests palladium-103 and cesium-131 as alternatives. Palladium-103 has the advantage of being an almost pure X-ray emitter of about 20-23 keV. Furthermore, it is compatible with the body in that it is substantially insoluble in the body. Thus palladium presents less of a potential hazard to the body, in the rare event of shell leakage, than does radioactive iodine, which if it were to leak from its encasing shell, would migrate to and accumulate in the thyroid with potentially damaging results.

Although the '049 patent suggests the use of seeds containing palladium-103, to date, only seeds containing iodine-125 have been commercially available. The reason that palladium-103 has not been used as an interstitial X-ray source is suggested in *Medical Physics Monograph No. 7*, "Recent Advances in Brachytherapy Physics", D. R. Shearer, ed., publication of the American Association of Physicists in Medicine, (1979) at page 19 where it is noted that its 17-day half-life (as compared with iodine-125 with about a 60-day half-life) is "just too short".

Indeed a 17-day half-life is difficult to work with in making capsules as produced according to the teachings of '049 patent in which substantially pure palladium-103 is contemplated. The short half-life represents a substantial obstacle to providing implants that contain substantially pure palladium-103. To produce substantially pure palladium-103, a transmutable element, such as rhodium-103, is converted to palladium-103 in a nuclear particle accelerator, and the palladium-103 is then isolated from untransmuted source material. The processing time of isolating the palladium-103 and additional processing time needed for encapsulating the radioactive material results in a substantial loss of activity of the palladium-103 before it is ever used in the body. Furthermore, producing palladium-103 by means of an atomic particle accelerator is difficult, and palladium-103 produced in this manner is very expensive. These considerations undoubtedly account for the fact that palladium-103 has not been incorporated in commercially available tumor treatment materials.

It is desirable to be able to use palladium-103 as an interstitially implantable X-ray source as the radiation spectrum of palladium-103 is somewhat more favorable relative to that of iodine-125. More importantly, the shorter half-life of palladium-103 relative to iodine-125, although presenting problems with respect to delivering the material to the patient, has important advantages with respect to patient care. The patient is significantly radioactive for a substantially shorter period of time and therefore poses less of a hazard to medical personnel and others who come in contact with the patient for the same period of time. By using a short half-life isotope for interstitial implantation, the time during which precautions against radiation exposure must be taken when treating the patient may be reduced, and the patient's periods of confinement in the hospital may be correspondingly reduced. As noted above, palladium does not present the potential problem of leaking iodine. Thus, it would be desirable to have methods and materials for making palladium-103 generally available as an implantable X-ray source.

A disadvantage of I-125-containing seeds, as presently produced, is that the seeds are anisotropic in their angular radiation distribution. This is due to the configuration of the capsules or seeds which are tubular and which, due to currently used shell-forming techniques, have large beads of encapsulating shell material at the sealed ends of the tubular structure. Although the '049 patent proposes unitary tubes that are sealed so as to have ends formed to be of substantially the same thickness as the sidewall of the tubular structure, the capsules actually produced by the assignee of the '049 patent have heavy beads of shell material at the ends of the seeds that result from the welding process. Such beads of material substantially shield emitted radiation, whereby the amount of radiation emitted from the ends of the capsule is substantially reduced relative to the amount of radiation emitted from the sidewall of the capsule. It would be desirable to produce implantable X-ray-emitting seeds with a more isotropic radiation distribution.

SUMMARY OF THE INVENTION

Interstitially implantable particles or capsules ("seeds") are produced containing palladium that has first been substantially enriched in palladium-102 and then subsequently exposed to high neutron flux so that a small, but significant, fraction of the palladium-102 is transmuted to X-ray-emitting palladium-103. The palladium is distributed on or throughout pellets of non-shielding carrier material, and the pellets are preferably encased in an outer shell which is stable and biocompatible within the body. An X-ray-opaque marker is generally also encapsulated within the shell along with the pellets to permit X-ray visualization of the location of implantation of the seed within the body. The palladium-102 may be activated by exposure to neutron flux either before or after its encasement in a shell. The palladium-102 is preferably activated after encapsulation, and an X-ray-opaque marker is selected which has acceptably low levels of isotopes that will be transmuted to isotopes which emit significant amounts of undesirable radiation.

In order to produce an outer shell for an implantable seed that emits a more isotropic radial distribution of radiation, end members are produced for interfitting with the ends of the tubes in which the pellets and markers are inserted. After application of the end members to the tube, the end members are laser-welded to the tube to establish a permanent sealing bond. The use of end members of substantially the same thickness as the tube itself reduces the bulk of material at the ends of the capsules and therefore does not absorb X-ray radiation emitted by palladium-103 to the extent that the bulk of material present in commercial capsules shields emitted X-ray radiation. Accordingly, the X-ray emissions from the seeds of the present invention are more isotropically radially distributed.

BRIEF DESCRIPTION OF THE DRAWINGS

FIG. 1 is a cut-away view of an implantable X-ray emitting capsule or seed, embodying various features of the present invention;

FIG. 2 is a cut-away view of an alternative embodiment of an implantable seed;

FIG. 3 is a perspective view, partially cut away of an alternative embodiment of the invention in the form of an implantable particle; and FIG. 4 is a perspective view, partially cut away, of a further embodiment of a particle according to the invention.

DETAILED DESCRIPTION OF THE PREFERRED EMBODIMENTS

Illustrated in FIG. 1 is a capsule or seed 10, embodying various features of the present invention, which is implantable at a selected site within a living body and emits localized X-ray radiation therein. The X-rays are emitted from a pair of pellets 14 of generally spherical shape. The pellets contain an X-ray-emitting material that is distributed on or throughout a carrier material that is substantially non-shielding of X-rays. Interposed between the two pellets 14 is a rod-shaped marker 18 which is formed of X-ray-opaque material and which provides a means of visualizing the seed 10 with an external X-ray apparatus after the seed has been implanted within the body. The pellets 14 and marker 18 are encased and sealed within an outer shell 22 formed of a short tube 24 and a pair of end members or caps 26 welded thereto.

In accordance with the invention, the X-ray-emitting material for an implantable particle or seed 10 is palladium which is substantially enriched in palladium-102 and which has been activated (transmuted) by exposure to neutron flux to contain a small, but significant, fraction of X-ray-emitting palladium-103. Palladium-103 is a nearly ideal source of X-rays for internal implantation because it has a very soft radiation spectrum, consisting primarily of low-energy X-ray (or low frequency gamma ray) emissions in the 20–23 keV range. The radiation spectrum of palladium-103 is even softer than the radiation spectrum of iodine-125, the currently preferred radioactive isotope for tumor treatment by permanent interstitial implantation. The approximately 17 (16.97) day half-life is short relative to the approximately 60-day half-life of iodine-125, decreasing the time during which the implanted seed poses some significant radiation danger to those who come into contact with the patient.

Although the benefits of palladium-103 for this purpose has been previously appreciated, the advantages of palladium-103 have not been truly realized because of the practical difficulties involved in providing palladium in active and implantable form to the patient. As noted above, the short half-life of palladium-103 makes it difficult to manufacture implantable particles of substantially pure palladium-103, which must be produced in a particle accelerator from transmutable isotopes and then isolated. By using palladium that is enriched in palladium-102 in the manufacture of seeds and then activating the palladium-102 in the neutron flux of a nuclear reactor to contain significant amounts of palladium-103 just prior to production of the seeds (in a hot manufacturing process) or subsequent to production of the seeds (in a cold manufacturing process), seeds having a controlled amount of palladium-103 can be provided to a patient before substantial decay of the short half-lived palladium-103 has occurred. A further, very significant advantage of using Pd-102-enriched palladium is that the palladium-103- activity can be regenerated if the seeds remain on the shelf too long prior to use.

A very important consideration in constructing a seed in which palladium-103 is the X-ray-emitting isotope is the self-shielding effect of palladium. That is, although palladium-103 emits X-rays, all of the isotopes of palladium absorb substantial amounts of X-rays. Naturally occurring palladium contains approximately 1.0 isotope percent of palladium-102 (and negligible amounts of palladium-103). Accordingly, if naturally occurring palladium were to be irradiated by neutron flux so as to convert a small, but significant, amount of the palladium-102 to palladium-103, the amount of X-rays actually emitted from the irradiated palladium would be very substantially reduced by the self-shielding.

In accordance with the present invention, the palladium that is used in the implantable seeds is substantially enriched in palladium-102; generally, the palladium is enriched in palladium-102 to at least about 50 atom percent and is preferably enriched to about 70 atom percent or upward in palladium-102. Thus, for the same activation of palladium-102 to palladium-103, the Pd-102-enriched palladium emits about two orders of magnitude more X-rays than irradiated naturally occurring palladium. Palladium can be enriched in palladium-102 by electromagnetic separations, and palladium that is enriched up to about 80% in palladium-102 may be obtained, for example, from Oak Ridge National Laboratories.

In the X-ray-emitting pellets depicted in FIG. 1, Pd-102-enriched palladium 14 is distributed in a carrier or base material which is substantially non-absorbing of X-rays. The distribution of the palladium throughout the pellets reduces the self-shielding effect of the palladium. Generally, low atomic weight (low Z) materials tend to be non-absorbing of electrons. The base material should be relatively non-toxic, for safety considerations in the unlikely event that a seed should leak. It should also be able to withstand the conditions of activation of palladium-102 by neutron flux, which generally is accomplished at relatively high temperatures within or adjacent to a nuclear reactor. Furthermore, the base material should not activate upon exposure to the activating radiation to produce isotopes which emit undesirable radiation. In this regard, potential impurities in the base material should be considered with regard to possible transmutation to undesirable isotopes. A preferred base material is highly purified aluminum which is preferably provided in powder form having average particle sizes of between about 40 and about 200 microns. Metallic Pd-102-enriched palladium is suitably deposited on aluminum powder surfaces, e.g., by chemical precipitation, and then the palladium-coated aluminum powder is pressed into spheres at pressures sufficient to achieve at least about 95% of theoretical density.

The amount of palladium in a pellet 14 depends upon the radiation dosage required for each seed. For a seed having a configuration as shown in FIG. 1, in which a pair of spherical pellets each approximately 0.6 mm in diameter are formed, each pellet will contain between about 0.01 and about 0.05 mg of Pd-102-enriched palladium, whereby the palladium activity of the seed immediately after activation will be between about 4 and about 12 mCi, without accounting for shielding factors, which will typically reduce the actual radiation by about 40%. If aluminum is used as the base material, the compressed spherical pellet contains about 2.6 gm of aluminum per cubic centimeter. Other low Z elements, such as Mg and C might also be used as the base material. Certain refractory materials, such as low Z glasses, $Al_2O_3$, BeO and $Mg_2O$ might also serve as base materials. Polymeric materials can also be used as base materials, providing they can withstand the conditions, particularly temperature, of palladium-102 activation.

In order to insure that the X-ray-emitting seeds 10 are implanted within a tumor and are distributed therein so as to adequately subject all of the tumorous tissue to meaningful X-ray radiation doses, it is desirable to visualize the implanted seeds by external means. Generally, this is accomplished by X-ray examination using an X-ray beam from an external (to the body) source. Accordingly, the seeds include the X-ray-opaque marker 18. Although the marker is highly shielding of the low-energy X-rays emitted by the palladium-103 in the pellets 14, the disposition of the opaque marker 18 between two X-ray-emitting pellets helps to assure that a substantially isotropic angular distribution of X-rays is emitted from the seeds.

The opaque marker 18 is generally a high Z metal. Above-identified U.S. Pat. No. 3,351,049 teaches the use of gold and tungsten as X-ray opaque markers. These materials are suitable markers for X-ray opaqueness; however, these materials contain isotopes which transmute to undesirable radioisotopes under the high neutron flux required for palladium-102 activation. Thus, these materials are to be avoided if the seeds are to be manufactured in a cold process and the palladium-102 then activated within the sealed seed and/or if it is contemplated to reactivate seeds which have been stored on the shelf for too long a time period during which natural radioactive decay substantially reduces the palladium-103 activity of the seed.

In accordance with a preferred aspect of the invention, the opaque marker 18 is formed of a material which does not contain isotopes that transmute to undesirable radioactive isotopes under palladium-102 to palladium-103 activation conditions. Suitable metals for this purpose include lead and rhodium. By selection of materials lacking undesirable transmutable isotopes, the seed may be produced by a cold manufacturing process, and the palladium-102 activated to contain palladium-103 subsequent to sealing the seed, and also, an intact seed can be reactivated by placing it back in the neutron flux generated by a nuclear reactor. Again, when selecting a suitable X-ray-opaque material, the transmutability of any impurities should be considered as well as the transmutability of isotopes of the marker element itself. For example, iridium, as an impurity, presents a particular problem with respect to the use of rhodium, which is otherwise a suitable marker material. If rhodium is used, iridium should be present as an impurity at 5 ppm or less. Antimony is an impurity frequently present with lead which should be minimized. 99.99% pure lead is commercially available, and at this time, represents the most inexpensive material that is suitable as an X-ray-opaque marker in an implantable tumor-treatment seed which is activated or reactivated after assembly. Pure, but non-enriched palladium might also be used as the marker.

An important advantage of using palladium enriched in palladium-102 is its ability to be activated to produce the desired radioactive isotope, i.e., palladium-103, by placing the palladium in a high neutron flux, such as that which is present in a nuclear reactor. Palladium-102 transmutes to palladium-103 through neutron capture. Generally, the only practical source of high neutron flux is a radiation beam from a nuclear reactor, which, of course, emits a mixture of radiation types. It may be desirable to use appropriate filters to enhance the neutron flux spectrum.

Transmutation of palladium-102 to palladium-103 occurs relatively slowly within a nuclear reactor neutron flux, and only a very small portion of the palladium-102 is converted to palladium-103 at any one time. After placing the palladium-102 in the reactor, the amount of palladium-103 begins to build up, more rapidly at first, and then more slowly until the rate of palladium-103 decay is equal to the rate of transmutation of palladium-102 to palladium-103. At the present time, an equilibrium between palladium-103 decay and palladium-102 transmutation is reached at a palladium-103 concentration of about one atom per several hundred palladium-102 atoms. Generally at about 1½ half-lives (22-23 days), the palladium-103 has reached a level of about 70% of its equilibrium value, and at about this point, the rate of increase of palladium-103 percentage is so slow that further exposure to radiation is generally not considered to be of substantial value.

Palladium-102 activation may be performed either after the seed is fully assembled in a cold process or just before the seed is finally assembled in a hot process. The cold process simplifies the manufacturing process of the seed in that no precautions against radiation exosure need to be taken during assembly because it is only after final assembly that the seed is made radioactive. In the cold process, activation is the final step, and therefore, the seeds can be used almost immediately, before substantial amounts of the palladium-103 has decayed. However, even using the hot process, where activation is performed on the palladium-in-aluminum pellets prior to their final assembly into the seeds, the final seed assembly may be performed relatively quickly, allowing the seeds to be provided at near maximum palladium-103 activity. Although the hot process requires apparatus for shielding technicians who assemble the seeds from radioactivity, the hot process has advantages in that there is substantially no concern about transmutation of isotopes present in other components of the seed as these are not exposed to any significant radiation flux. Thus, in the hot process the marker and other components may be made without concern as to the transmutability of isotopes in the components, either as major component materials or as impurities in component materials.

Providing that the seed is manufactured of materials that do not contain unacceptable amounts of isotopes that transmute to dangerously radioactive isotopes, an important advantage of a seed containing Pd-102-enriched palladium is its ability to be reactivated by again placing the seed in high neutron flux, e.g., in a radiation beam produced by a nuclear reactor. The short half-life of palladium-103 gives the seeds a correspondingly short shelf-life. The seeds are generally intended for use within three weeks and preferably not before one week. The activity of palladium-103 after a week is about 75% of its initial value, and its activity after three weeks is about 42% of its initial value.

The cold manufacturing of palladium seeds involves irradiation of the seed after the components are assembled and welded. As a result, the titanium capsule, the lead marker and the aluminum ball carrier for the palladium-103 are all also irradiated. Commercially available materials contain trace impurities which are activated by the neutron field of the nuclear reactor. The structural materials themselves also are activated by the neutrons; however, all but one of the activities produced in such structural materials are short-lived and will have decayed to negligible levels seven days after completion of the irradiation. That particular activated isotope is scandium-46 (Sc-46) which is produced by the fast neutron (n,p) reaction with titanium-46. The properties of this isotope are: half life 83.8 days; beta energy 0.357 Mev; and gamma energies 1.105 and 0.889 Mev. Because the maximum practical range of the beta particles is about 0.07 cm in tissue, they have little therapeutic significance, especially because only a fraction gets out of the seed itself.

By adjusting the amount of Pd-102 included in a seed, the time duration of irradiation, and the ratio of fast to thermal neutron flux at the irradiation position, the combined mCi of Sc-46 and trace contaminants present seven days after completion of irradiation can be held to less than 0.4% of the mCi (comp.) of the Pd-103. Because the specific dose rate factor for the Sc-46 is 8 times that of Pd-103, the Sc-46 plus other impurity radiation dose rate delivered at one week is approximately $8 \times 0.4\% = 3.2\%$ of that from the Pd-103. Although the sum of longer-lived trace isotopes has some effect on dose rate after several months, at two years, the total activity of a Pd-103 seed is less than 100 nanocuries.

In this field of medicine, it may be useful to coordinate seed manufacture with patient treatment scheduling. Although seeds can be used at any time, according to the residual palladium-103 activity as can be charted from the natural decay period of the isotope, it is impractical to use multiple seeds in which the palladium-103 has decayed to a very low percent of initial activity in place of a lesser number of freshly activated seeds. Due to the cost of Pd-102-enriched palladium, the seeds are relatively expensive to produce, and it is preferred to reactivate seeds that have spent too much time on the shelf. Although the seeds may be ordered by a treatment center and manufactured or activated correlating to the expected time of patient treatment, events, such as a cancelled treatment, may result in seeds sitting on the shelf for too long. If this happens, the treatment center may return the seeds to the manufacturer for reactivation, the cost of reactivation being quite small relative to the cost of initially manufacturing the seeds themselves. As the content of palladium-102 has not been measurably diminished, reactivated seeds have essentially the same activity as newly manufactured seeds.

Of course, if seeds have been manufactured by a hot process so that the seed components were selected without regard for their isotope content, the seeds may not be feasibly reactivated. Nevertheless, the pellets may be removed from the seeds, reactivated and used to remanufacture additional seeds. The ability to reactivate Pd-102-enriched palladium represents an advantage of palladium relative to iodine as an X-ray source, as iodine cannot be similarly activated to iodine-125.

The outer shell 22, wherein the radioactive pellets 14 and the opaque marker 18 are contained, is formed of a material which is biocompatible and stable within the body. The material should be relatively non-absorbing of low energy X-rays. A preferred shell material is titanium. If the seed is to be manufactured by a cold process and/or if it is expected that the seed might have to be reactivated, it is preferred to use highly purified titanium containing only acceptable amounts of elements transmutable to undesireable radioactive isotopes. In particular, iron, cobalt and europium, commonly found as impurities in titanium, should be minimized. A suitably pure, commercially available titanium is ASTM B265-78, Grade 2, having an iron content less than 0.05%.

In accordance with one important aspect of the present invention, the outer shell 22 of the seed 10 is constructed from a three-piece assembly, including the tube 24 and the pair of end caps 26 that are welded to the tube 24 after the other components, i.e., the X-ray-emitting pellets 14 and the X-ray-opaque marker 18 are inserted into the tube. The important advantage of this construction relative to the construction of the shells of seeds presently in production is that it permits the formation of thinner ends, i.e., about the same thickness as the sidewalls, and thereby provides for a better angular distribution of the emitted X-rays. Even though the shell material is selected to be as transparent to X-rays as is consistent with other requirements of the shell material, the shell will absorb some of the low-energy X-rays emitted by the palladium-103. In prior art seeds that were formed from a single tublar piece welded shut or otherwise closed at its ends, there generally results a bead of material at each end having a large thickness relative to the tubular sidewall. Typically, the end beads in currently produced seeds are about ten to fifteen times the thickness of the tubular sidewall. A relatively massive end bead absorbs significant proportions of the incident X-ray radiation at the ends of the seeds, causing the angular distribution of X-rays from such beads to be uneven. Thus the X-ray dosage to adjacent tumor tissue is dependent upon the orientation at which the seed is implanted, which orientation is generally random. By using end caps 26 having the same thickness as the tube 24, the end of the shell 22 is as thick as the sidewalls of the shell, promoting the generally isotropic angular distribution of X-rays from the seed. In the seed illustrated in FIG. 1, the end caps are cup-shaped, including a circular end wall 27 and an outwardly extending cylindrical sidewall 29. The diameter of the end caps 26 is proportioned to fit closely within the ends of the tube of the seed. After the seed 10 is assembled, the end caps 26 are welded, e.g., with a laser, to the tube 24, thereby permanently sealing the pellets 14 and the marker 18 within the shell. Although this construction produces double-walled sections extending outwardly of the circular end walls 27 of the end caps; a double-walled thickness is less than the thickness of end beads in currently produced seeds, and the double-walled segment results in additional shielding only along a narrow angular region.

It should be noted that although the palladium has been described as being incorporated in the pellet in elemental (metallic) form, there is no requirement that the palladium be in elemental form. As the palladium-103 will decay at the identical rate, regardless of whether it is in elemental form or whether it is incorporated as a compound or alloy, the palladium may be provided compounded or alloyed with other elements. Indeed, in manufacturing the pellet described with respect to FIG. 1, some of the palladium will oxidize. The element or elements with which palladium compounds should be substantially non-shielding, and in this respect, low Z elements are preferred. Furthermore, the compounding element or elements should have controlled low levels of isotopes, which transmute to undesirable radioisotopes in the neutron flux to which the palladium is exposed for activation. It is further desirable that if a palladium compound or alloy is used as the X-ray-emitting source, the compound or alloy be substantially insoluble in aqueous solutions to prevent transfer of radioactive palladium throughout the body in the unlikely event of breach of the shell. A reason for providing the palladium as a palladium compound or alloy is to facilitate its incorporation and even distribution in a particular base material. For example, a suitable ceramic pellet might be formed of aluminum oxide with palladium oxide homogeneously distributed therein.

In a similar manner, the high Z materials which serve as markers may be provided in compound form as well as metallic form. As it is the nuclei of high Z materials that are primarly responsible for their X-ray-opaqueness, it is generally immaterial which form marker materials take. If the marker materials are provided in compound form, similar considerations with respect to transmutability of compounding elements and solubility apply. Generally, however, metallic marker materials, such as lead or rhodium, are used in their elemental forms which are relatively inexpensive and are easy to shape into appropriate marker configurations.

Illustrated in FIG. 2 is an alternative embodiment of a seed 10', in which the end caps 26' have sidewalls 29' that are proportioned to overfit the ends of the tube 24 and then are laser welded thereto. Otherwise the components, including the pellets 14, marker 18 and tube 24 are as described with reference to the FIG. 1 embodiment.

The invention will now be described in greater detail by way of specific example.

EXAMPLE

Commercially pure powdered aluminum having an average particle size of about 150 microns is obtained from Leico Industries, Inc. Palladium that is 74% enriched in palladium-102 is obtained from Oak Ridge National Laboratories. The palladium is coated on the aluminum powder by chemical precipitation, approximately 50 micro grams of palladium being used to coat 0.57 milligrams of aluminum powder. The coated powder is placed in a mold and pressed to 95% theoretical density at room temperature to produce compacted pellets 0.6 mm in diameter, each containing about 25 micrograms of palladium. 1.5 mm long sections are cut from a 0.4 mm in diameter, 99.99% pure lead rod for use as a radioactive marker.

ASTM B265-78, grade 2 titanium with iron content less than 0.05% is used to form tubular sections, 4.5 mm in length, 0.8 mm in outside diameter and 0.7 mm inside diameter (0.05 mm wall thickness). The same titanium is used to form end caps, 0.7 mm long, OD 0.7 mm, ID 0.6 mm., wall thickness (including end walls) of 0.05 mm.

The seed is constructed by inserting two pellets 14 in the tube 24 segment flanking a marker 18 formed of a lead rod segment, inserting the caps in the ends of the tube and laser-welding the end caps to the tube.

The seeds are placed in the University of Missouri nuclear reactor at Columbia, Mo. which provides a neutron flux of about $4 \times 10^{14}$ nv. Activation continues of a period of 21 days.

At this time, palladium-103 as a percentage of palladium-102 is about 58% of its equilibrium value, i.e., that percentage which would eventually be reached by extended exposure to neutron flux in the nuclear reactor. The total radiation level emitted by the palladium-103 within the two pellets in each seed is about 6.8 mCi; however, the X-ray activity of the seed is more correctly stated in a compensated value of mCi. The compensated value takes into effect the self-absorption of approximately 40% within the seed. The compensated mCi value of the seed is 4.1 mCi. Allowing 7 days for decay of short-lived isotopes and for delivery to a hospital, the compensated activity is about 3.1 mCi. By adjusting the amount of palladium in the seeds, the compensated activity level of the seed can be easily adjusted to between about 0.5 and about 5 mCi. The moderately anisotropic dose pattern of the palladium seed means the seed may be modeled approximately as a point source of X-ray activity.

The small size of the palladium seeds permit them to be implanted with a minimum of tissue trauma. They may be injected through a #17 gauge needle or may be implanted using established applicators, including Scott, Mick and Henschke applicators.

Seeds containing palladium-103 as the X-ray-emitting isotope have inherent advantages relative to other isotopes which have been used for interstitial implantation. Unlike iridium-192, gold-198 or radon-222 and like iodine-125, it emits neither alpha or beta particles. Its gamma or X-ray radiation energy is lower than any of these. As a consequence, its radiation is attenuated by half in tissue at 1.0 cm and is attenuated by half in 0.008 mm lead. Thus, the action of palladium-103 radiation is more localized within a tumor, does little damage to surrounding tissue and is almost completely attenuated within the body. Also, the radiation emitted by palladium-103 is easily shielded by lead and a major portion of palladium-103-emitted X-rays may be shielded with thin lead foils that are incorporated in clothing or the like. Clinical evidence has shown that for obtaining an 80% tumor control rate in several types of tumors, 16,000 rads is needed from a 60-day half-life I-125 source. The characteristics of the emitted radiation from the Palladium Seed (20-23 key) should yield a similar therapeutic effect as the I-125 Seed (27-35 kev); hence, the same tumor control results are expected with only 11,500 Rads from Pd-103. This is because a higher dose rate delivered over a shorter period has the same radiobiological effect of an equivalent lower dose rate delivered for a longer time. When radiation is delivered at a low dose rate, and the treatment time is extended to a point where it is long compared with the cellular repair half-time, then a substantial proportion of the sublethal damage may be repaired during the exposure. The resultant low dose-rate survival curve will be shallower than that characteristic of acute exposures.

Palladium seeds may be indicated for tumors with the following characteristics: localized, unresectable and having low to moderate radiosensitivity. The tumors may be of the following type: superficial; intrathoracic; intraabdominal; lung, pancreas, prostate(Stage A or B); residual following external radiation or recurrent.

The palladium seed has many inherent benefits for the patient. The palladium-103 isotope was selected because of its soft therapeutic X-rays and 17-day half-life. The low energy X-rays benefit the hospitalized patient due to the simplified radiation protection requirements which may eliminate the need for expensive isolated accomodations. The relatively short half-life (17-days) minimizes the time which a patient is walking around with a radioactive source in his/her body. There should be fewer restrictions on the release of the patient from the hospital due to the low gamma energy (20-23 kev) and moderate half-life of 17-days. The release of patients from the hospitals is based upon the exposure rate at one meter from the patient, according to the recommendation in Handbook NCRP 37. If there is the rare occurance a palladium seed leaking, the biologically inert components of the seed represent little or no toxicity danger to the patient.

Permanent implants are normally quicker and simpler to execute than removable implants. Risk of infection, radiation exposure and surgical complications are normally reduced through the use of permanent implants.

Palladium seeds also benefit medical personnel and others who come into contact with the patient. At many hospitals where high gamma energy implants were being performed, the accumulated exposure to the medical personnel gave a reason for concern. High energy gamma isotopes include radon-222 and gold-198 which cannot be sufficiently shielded to protect medical personnel during implantation procedures. Palladium seeds emit low energy gamma (20-23 kev) X-rays which are easily shielded by any high Z material, yet still maintain effective penetration in low Z tissue. Greater than 97% of the radiation emitted by the palladium seed can be shielded by only a 0.06 mm. thick lead foil. This allows the use of lead-impregnated vinyl gloves and bandages to reduce the radiation exposure from handling the seeds to a minimum. Thin metal shields and lead glass screens are commercially available to provide protection for the technicians preparing the palladium seeds for implant. When reasonable precautions are taken, i.e., handling seeds with forceps, lead impregnated gloves, thin lead wrappings over an implanted superficial tumor dressing, medical personnel can expect to receive very little exposure.

Palladium seeds have the inherent advantage that the capsules, if ruptured, present little or no biological hazard due to the nontoxic nature of all the components.

The implantable seeds provide the palladium to the tumor in a manner that provides several advantages. By distributing the palladium in the aluminum or alternative base material of the pellets, the self-shielding effect of the palladium is reduced, thereby achieving a greater compensated radioactivity than would be provided by corresponding amounts of a dense mass of Pd-102-enriched palladium. By encapsulating the pellets and the radioactive marker in a non-toxic shell, any toxic effects of the base material, e.g., aluminum, and the X-ray marker, e.g., lead, may generally be ignored. Even in the rare event of breach of the shell, allowing body fluids to gradually seep into the shell, there would be very slow transfer of any dissolved base material or marker material from the breached shell. Seeds that are to be implanted receive X-ray and microscopic inspection and are tested for leaks of the shell before shipment, substantially assuring that the shell will not be breached subsequent to implantation. The format of the seeds have the further advantage of being similar in format to the seeds presently used to interstitially administer iodine-125, and therefore, should readily gain acceptance by both government regulators and users, e.g., physicians.

Although the seed form of palladium administration represents a preferred form of administration, the palladium might be administered in other manners. Illustrated in FIG. 3 is an implantable particle 50 which has several of the advantages of the seed described above. In this embodiment, Pd-102-enriched palladium in metallic form is distributed as an outer layer 52 over the surface of a metallic palladium core 54 of natural isotropic distribution. The core 54 serves as an X-ray marker for external visualization, whereas the distribution of a small amount of Pd-102-enriched palladium over the surface of the core makes efficient use of the expensive enriched palladium and provides a very isotropic distribution of emitted X-rays. Although the X-rays emitted inward to the core are substantially completely absorbed, substantial amounts of the low-energy X-rays emitted by the palladium-103 of the surface layer are directed outwardly to the tumorous tissue.

Illustrated in FIG. 4 is another particle 70 which might be similarly used to administer palladium to a tumor site. In this embodiment, the Pd-102-enriched palladium in either metallic or compound form is dispersed as particulates 72 in a layer 74 of biocompatible, low-shielding ceramic base material, which, in turn, is formed around a spherical center 76 formed of or containing high Z material, such as lead, rhodium, gold or tungsten and which serves as an X-ray marker. The dispersion of the enriched palladium reduces self-shielding of the palladium-103-emitted X-rays. The base material might also be a non-toxic, low-shielding, metal or polymer.

In particles of the type described with reference to either FIG. 3 or FIG. 4, the particle size should be at least about 0.5 mm in diameter to assure retention at the tumor site. Implantable particles are generally not more than about 2 mm in diameter as larger sizes are difficult to administer and might cause unnecessary irritation. For purposes of this invention it is generally desired that at least about 30% of the X-rays generated by decay of palladium-103 actually be emitted from the implantable particle, and it is preferred that upwards of 50% be emitted.

While the invention has been described in terms of certain preferred embodiments, modifications obvious to one with ordinary skill in the art may be made without departing from the scope of the invention. For example, whereas seeds are described herein as preferably containing an X-ray marker for external visualization, it is to be understood that other methods of visualizing internal organs and materials are coming into increasing use, including CAT scanning and NMR scanning. If visualization of the tumor and the seeds therein is contemplated by another method than by X-ray, the seed should be detectable by these visualization techniques, for example, by inclusion of a marker particularly adapted for visualization by one of these techniques.

Various features of the invention are set forth in the following claims.

What is claimed is:

1. A seed for implantation into a tumor within a living body to emit X-ray radiation thereto comprising at least one pellet that contains palladium enriched in palladium-102 to contain many times the amount naturally present, said palladium-102 being activatable by exposure to neutron flux so as to transform a portion of said palladium-102 to an amount of X-ray emitting palladium-103 sufficient to provide a radiation level measured as compensated mCi of greater than 0.5, and a shell of biocompatible material encapsulating said at least one pellet, said biocompatible material being selected from a material that is penetratable by X-rays in the 20-23 kev range.

2. An implantable seed according to claim 1 wherein said seed includes a base material and wherein said Pd-102-enriched palladium is distributed on or throughout said base material, the distribution of said Pd-102-enriched palladium on or throughout said base material ensuring that at least about 30% of the X-rays generated by the palladium-103 will be emitted from said particle.

3. An implantable seed according to claim 2 wherein said base material comprises compacted aluminum powder.

4. An implantable seed according to claim 1 wherein said seed also includes an X-ray-opaque marker within said shell for external visualization of said particle after its implantation in the body.

5. An implantable seed according to claim 4 wherein the material forming said X-ray-opaque marker is selected from the group consisting of lead, rhodium and palladium.

6. An implantable seed according to claim 4 wherein said shell has a generally tubular configuration, said marker is generally centrally located, and said at least one pellet includes two pellets, with one pellet disposed on either side of said marker to help promote a generally isotropic distribution of X-rays emitted from said particle.

7. An implantable seed according to claim 4 wherein said marker is formed of a material selected from the group consisting of lead, rhodium and palladium.

8. An implantable seed according to claim 1 wherein said shield is formed of titanium that contains no more than 0.05 percent iron.

9. An implantable seed according to claim 1 wherein said palladium is enriched to include at least about 50% in palladium-102.

* * * * *

UNITED STATES PATENT AND TRADEMARK OFFICE
CERTIFICATE OF CORRECTION

PATENT NO. : 4,702,228

DATED : October 27, 1987

INVENTOR(S) : John L. Russell, et al.

It is certified that error appears in the above-identified patent and that said Letters Patent is hereby corrected as shown below:

Column 1, line 55, change "Interstatial" to --Interstitial--.

Column 2, line 65, change "assigness" to --assignees--.

Column 4, line 47, delete "-" (dash) second occurrence.

Column 6, line 5, change "X-ray opaque" to --X-ray-opaque--.

Column 7, line 9, correct the spelling of --exposure--.

Column 8, line 51, correct the spelling of --undesirable--.

Column 9, line 5, correct the spelling of --tubular--.

Column 9, line 66, correct the spelling of --primarily--.

Column 10, line 24, change "micro grams" to --micrograms--.

Column 10, line 46, change "of" (first occurrence) to --for--.

Column 11, line 22, "key" should be --kev--.

Column 14, line 1, change "X-ray emitting" to --X-ray-emitting--.

UNITED STATES PATENT AND TRADEMARK OFFICE
CERTIFICATE OF CORRECTION

PATENT NO. : 4,702,228

DATED : October 27, 1987

INVENTOR(S) : John L. Russell, et al

It is certified that error appears in the above-identified patent and that said Letters Patent is hereby corrected as shown below:

Column 14, line 37, change "shield" to --shell--.

Signed and Sealed this

Twelfth Day of July, 1988

Attest:

DONALD J. QUIGG

Attesting Officer

Commissioner of Patents and Trademarks